United States Patent
Nichogi

(10) Patent No.: US 10,561,471 B2
(45) Date of Patent: Feb. 18, 2020

(54) MANIPULATOR

(71) Applicant: OLYMPUS CORPORATION, Tokyo (JP)

(72) Inventor: Masao Nichogi, Kanagawa (JP)

(73) Assignee: OLYMPUS CORPORATION, Tokyo (JP)

( * ) Notice: Subject to any disclaimer, the term of this patent is extended or adjusted under 35 U.S.C. 154(b) by 279 days.

(21) Appl. No.: 15/667,165

(22) Filed: Aug. 2, 2017

(65) Prior Publication Data

US 2017/0325903 A1 Nov. 16, 2017

Related U.S. Application Data

(63) Continuation of application No. PCT/JP2016/051360, filed on Jan. 19, 2016.

(30) Foreign Application Priority Data

Feb. 5, 2015 (JP) ................. 2015-021241

(51) Int. Cl.
*B25J 3/00* (2006.01)
*A61B 34/00* (2016.01)
(Continued)

(52) U.S. Cl.
CPC .............. *A61B 34/70* (2016.02); *A61B 17/00* (2013.01); *A61B 17/2909* (2013.01);
(Continued)

(58) Field of Classification Search
CPC . A61B 17/2909; A61B 18/1445; A61B 34/71; A61B 2017/00424;
(Continued)

(56) References Cited

U.S. PATENT DOCUMENTS

| 6,428,530 B1 | 8/2002 | Matern et al. |
| 2002/0040217 A1 | 4/2002 | Jinno |

(Continued)

FOREIGN PATENT DOCUMENTS

| EP | 1584300 A2 | 10/2005 |
| EP | 1 842 491 A2 | 10/2007 |

(Continued)

OTHER PUBLICATIONS

Extended Supplementary European Search Report dated Jul. 6, 2018 in European Patent Application No. 16 74 6405.6.
(Continued)

*Primary Examiner* — George J Ulsh
(74) *Attorney, Agent, or Firm* — Scully, Scott, Murphy & Presser, P.C.

(57) ABSTRACT

A manipulator including an elongated shaft, a distal-end treatment section disposed at a distal end of the shaft, a distal-end articulated section having a bendable joint and a rotatable joint, and a proximal-end operating section disposed at a proximal end side of the shaft, wherein the bendable joint has an axis intersecting a longitudinal axis of the shaft, the rotatable joint has an axis that intersects the axis of the bendable joint and that is substantially aligned with a central axis of the distal-end treatment section, the proximal-end operating section includes a first operating section gripped by one hand and causing the bendable joint to move about the axis intersecting the longitudinal axis of the shaft, and also includes a second operating section provided in the first operating section and causing the rotatable joint to move.

2 Claims, 8 Drawing Sheets

(51) Int. Cl.
*A61B 90/00* (2016.01)
*A61B 17/00* (2006.01)
*A61B 17/29* (2006.01)
*A61B 18/14* (2006.01)
*A61B 18/00* (2006.01)

(52) U.S. Cl.
CPC .......... *A61B 18/1445* (2013.01); *A61B 34/71* (2016.02); *A61B 90/00* (2016.02); *B25J 3/00* (2013.01); *A61B 2017/00331* (2013.01); *A61B 2017/00424* (2013.01); *A61B 2017/00438* (2013.01); *A61B 2017/291* (2013.01); *A61B 2017/2908* (2013.01); *A61B 2017/2929* (2013.01); *A61B 2018/0094* (2013.01); *A61B 2018/00922* (2013.01)

(58) Field of Classification Search
CPC .. A61B 2017/00438; A61B 2017/2908; A61B 2017/291; A61B 2017/2929; A61B 34/70; A61B 17/00; A61B 90/00; A61B 2017/00331; A61B 2018/00922; A61B 2018/0094; B25J 1/08; B25J 3/00
See application file for complete search history.

(56) References Cited

U.S. PATENT DOCUMENTS

| | | |
|---|---|---|
| 2004/0267406 A1 | 12/2004 | Jinno |
| 2005/0222587 A1 | 10/2005 | Jinno et al. |
| 2006/0167589 A1 | 7/2006 | Jinno |
| 2006/0190034 A1 | 8/2006 | Nishizawa et al. |
| 2007/0208375 A1 | 9/2007 | Nishizawa et al. |
| 2007/0221701 A1 | 9/2007 | Ortiz et al. |
| 2007/0225562 A1 | 9/2007 | Spivey et al. |
| 2007/0276430 A1 | 11/2007 | Lee et al. |
| 2008/0232932 A1 | 9/2008 | Jinno |
| 2009/0054734 A1* | 2/2009 | DeSantis ................ A61B 1/008 600/153 |
| 2010/0228283 A1 | 9/2010 | Jinno |
| 2011/0144430 A1 | 6/2011 | Spivey et al. |
| 2012/0130356 A1 | 5/2012 | Barrier et al. |
| 2012/0130401 A1 | 5/2012 | Barrier et al. |
| 2012/0234893 A1 | 9/2012 | Schuckmann et al. |
| 2012/0253324 A1 | 10/2012 | Lee et al. |
| 2012/0283748 A1 | 11/2012 | Ortiz et al. |
| 2013/0012931 A1 | 1/2013 | Spivey et al. |
| 2013/0197556 A1 | 8/2013 | Shelton, IV et al. |
| 2013/0282051 A1 | 10/2013 | Jinno |
| 2015/0012010 A1 | 1/2015 | Adler et al. |
| 2015/0090759 A1 | 4/2015 | Spivey et al. |
| 2017/0112519 A1 | 4/2017 | Inoue |

FOREIGN PATENT DOCUMENTS

| | | |
|---|---|---|
| EP | 1 842 501 A2 | 10/2007 |
| JP | 2002-102248 A | 4/2002 |
| JP | 2005-312919 A | 11/2005 |
| JP | 2006-116194 A | 5/2006 |
| JP | 2007-130485 A | 5/2007 |
| JP | 2007-325936 A | 12/2007 |
| JP | 2008-132352 A | 6/2008 |
| JP | 2009-538186 A | 11/2009 |
| JP | 2010-201005 A | 9/2010 |
| JP | 2014-515636 A | 7/2014 |
| JP | 2016-016238 A | 2/2016 |
| WO | WO 2007/139734 A2 | 12/2007 |
| WO | WO 2012/125618 A1 | 9/2012 |
| WO | 2015/002744 A1 | 1/2015 |

OTHER PUBLICATIONS

International Search Report dated Apr. 5, 2016 issued in PCT/JP2016/051360.

* cited by examiner

MANIPULATOR

CROSS-REFERENCE TO RELATED APPLICATIONS

This application is a Continuation Application of International Application No. PCT/JP2016/051360 filed on Jan. 19, 2016, which claims priority to Japanese Application No. 2015-021241 filed on Feb. 5, 2015. The contents of International Application No. PCT/JP2016/051360 and Japanese application No. 2015-021241 are hereby incorporated herein by reference in their entirety.

Technical Field

The present invention relates to manipulators.

Background Art

A known manipulator in the related art is of a type provided with a motor for driving a distal-end movable section and a grip handle at the proximal end of a coupling shaft, and the grip handle is provided with a knob and a lever that can be operated with the thumb of the hand gripping the grip handle (for example, see PTL 1).

Another known manipulator changes the orientation of a distal-end treatment section, which is provided at the distal end of a shaft and is moved in two-degree-of-freedom, namely, rotation and bending, in accordance with the orientation, serving as an operation input, of the wrist of the hand gripping an operating section provided at the proximal end of the shaft (for example, see PTL 2).

CITATION LIST

Patent Literature

{PTL 1}
Japanese Unexamined Patent Application, Publication No. 2010-201005
{PTL 2}
The Publication of Japanese Patent No. 4014792

SUMMARY OF INVENTION

An aspect of the present invention provides a manipulator including: an elongated shaft; a distal-end treatment section disposed at a distal end side of the shaft; a bendable joint provided in the shaft and has a tilting axis which is parallel to an intersecting direction intersecting a longitudinal axis of the shaft; a rotatable joint provided at a distal-end treatment section side relative to the bendable joint in the shaft, and having a rotational axis which is substantially aligned with a central axis of the distal-end treatment section; a handle disposed at a proximal end of the shaft, and connected to the shaft so that the handle can be tilted about a tilting axis which is parallel to the intersecting direction; a rotation operating section which is provided in the handle and which causes the rotatable joint to move; and a driving unit which moves the bendable joint in accordance with tilting of the handle, wherein the handle has a proximal end surface which is disposed at a proximal end side relative to the proximal end of the shaft in the longitudinal direction of the shaft, wherein a distance in the longitudinal direction between the proximal end surface of the handle and the tilting axis is set to be a distance which allows the tilting axis of the handle is disposed in one hand of an operator gripping the handle when the handle is gripped by the one hand in a state in which a palm of the one hand is close to the proximal end surface of the handle with a hand position where the longitudinal axis of the shaft extends through the palm of the one hand of the operator.

DESCRIPTION OF EMBODIMENT

A manipulator 1 according to an embodiment of the present invention will be described below with reference to the drawings.

Figure 1:
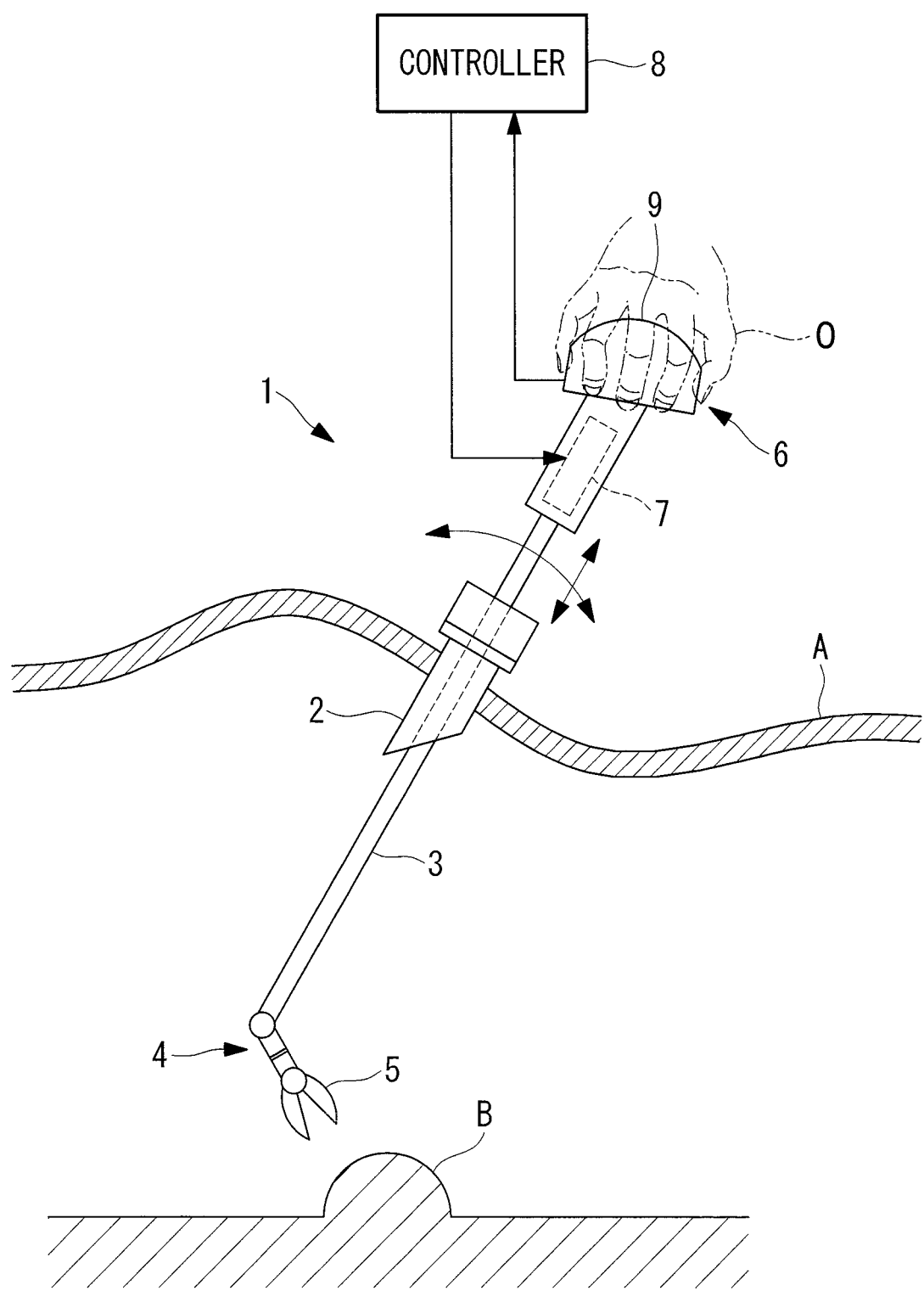
FIG. 1 illustrates the overall configuration of a manipulator according to an embodiment of the present invention.

As shown in FIG. 1, a manipulator 1 according to this embodiment is used in, for example, laparoscopic surgery and includes an elongated shaft 3 to be inserted through a trocar 2 pierced through the skin A, a distal-end articulated section 4 disposed at the distal end of the shaft 3, a distal-end treatment section 5 disposed at the distal end of the distal-end articulated section 4, a proximal-end operating section 6 that is disposed at the proximal end of the shaft 3 and that is to be operated by an operator O, a driving unit 7 that drives the distal-end articulated section 4, and a controller 8 that controls the driving unit 7 in accordance with an operation performed on the proximal-end operating section 6.

Figure 2:
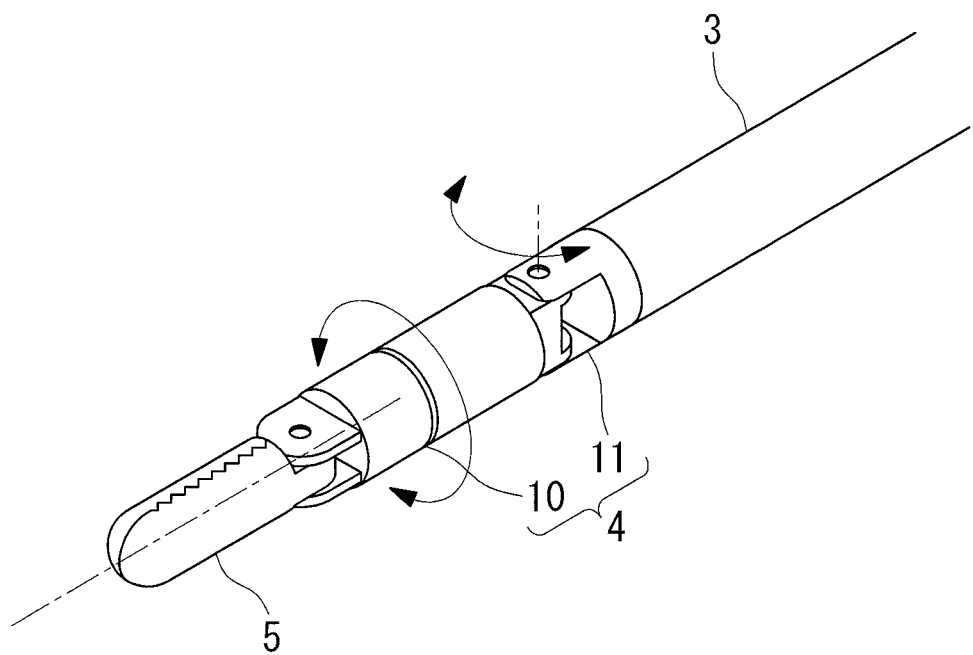
FIG. 2 is a perspective view illustrating a distal-end articulated section and a distal-end treatment section of the manipulator in FIG. 1.

The shaft 3 is formed of a rigid cylindrical material through which wires and cables (not shown) for driving the distal-end articulated section 4 and the distal-end treatment section 5 extend inside the shaft 3. In an example shown in FIG. 2, the distal-end articulated section 4 includes, in the following order from the proximal end, a bendable joint 11 that supports a distal end portion including the distal-end treatment section 5 in a tiltable manner about an axis orthogonal to the longitudinal axis of the shaft 3 and a rotatable joint 10 that supports the distal end portion in a rotatable manner about an axis aligned with a substantially central axis of the distal-end treatment section 5. The distal-end treatment section 5 is, for example, gripping forceps or energy forceps for medically treating an affected area B inside the body.

Figure 3:
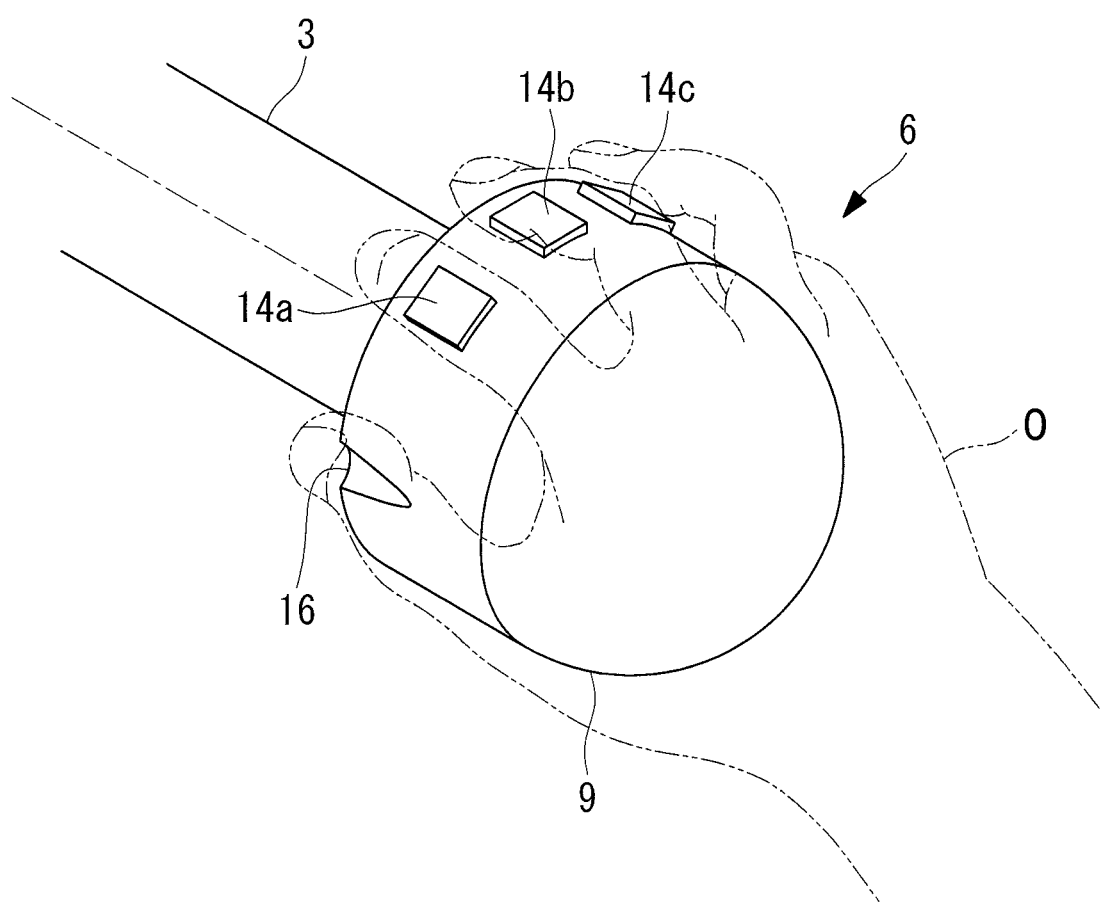
FIG. 3 is a perspective view illustrating a proximal-end operating section of the manipulator in FIG. 1.

As shown in FIG. 1, the proximal-end operating section 6 includes a substantially semispherical handle (first operating section) 9 attached to the proximal end of the shaft 3. The handle 9 has an outer diameter large enough to allow the operator O to bring the palm of one hand close to substantially the center of the substantially semispherical surface and to grip the handle 9 by setting his/her five fingers around the outer peripheral surface. Consequently, as shown in FIG. 3, when the operator O grips the handle 9, the palm of one hand gripping the handle 9 is set at a position through which the longitudinal axis of the shaft 3 extends.

Figure 4:
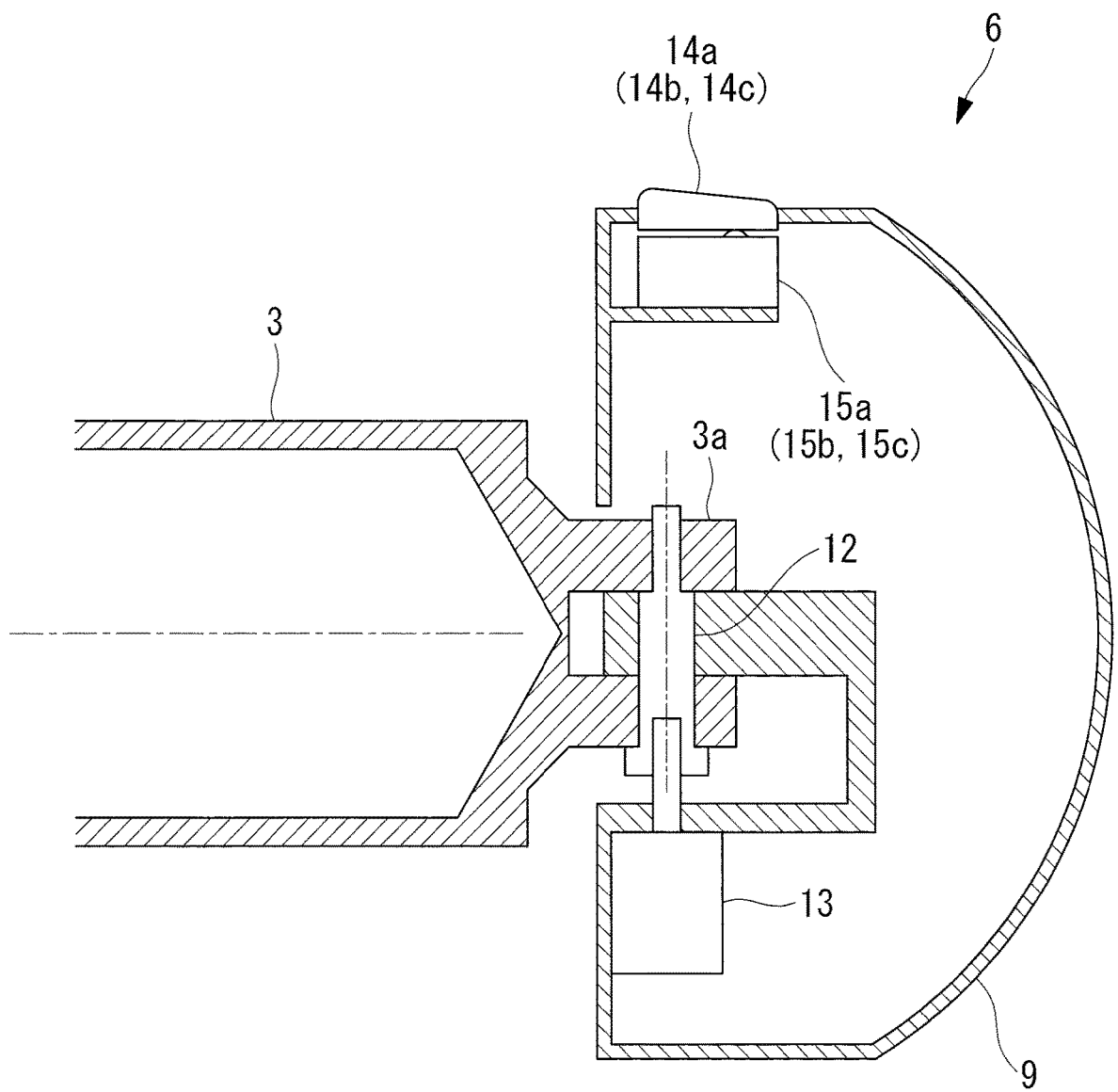
FIG. 4 is a vertical sectional view illustrating the proximal-end operating section and a shaft in FIG. 3.

As shown in FIG. 4, the handle 9 is coupled to a bracket 3*a*, provided at the proximal end of the shaft 3, in a tiltable manner about a tilt shaft 12 having an axis that is orthogonal to the longitudinal axis of the shaft 3 and that is substantially parallel to the axis of the bendable joint 11. When the operator O grips the handle 9, the tilt shaft 12 is disposed inside the one hand gripping the handle 9. Furthermore, the handle 9 includes an encoder 13 that detects the tilt angle of the handle 9 relative to the shaft 3.

Figure 5:
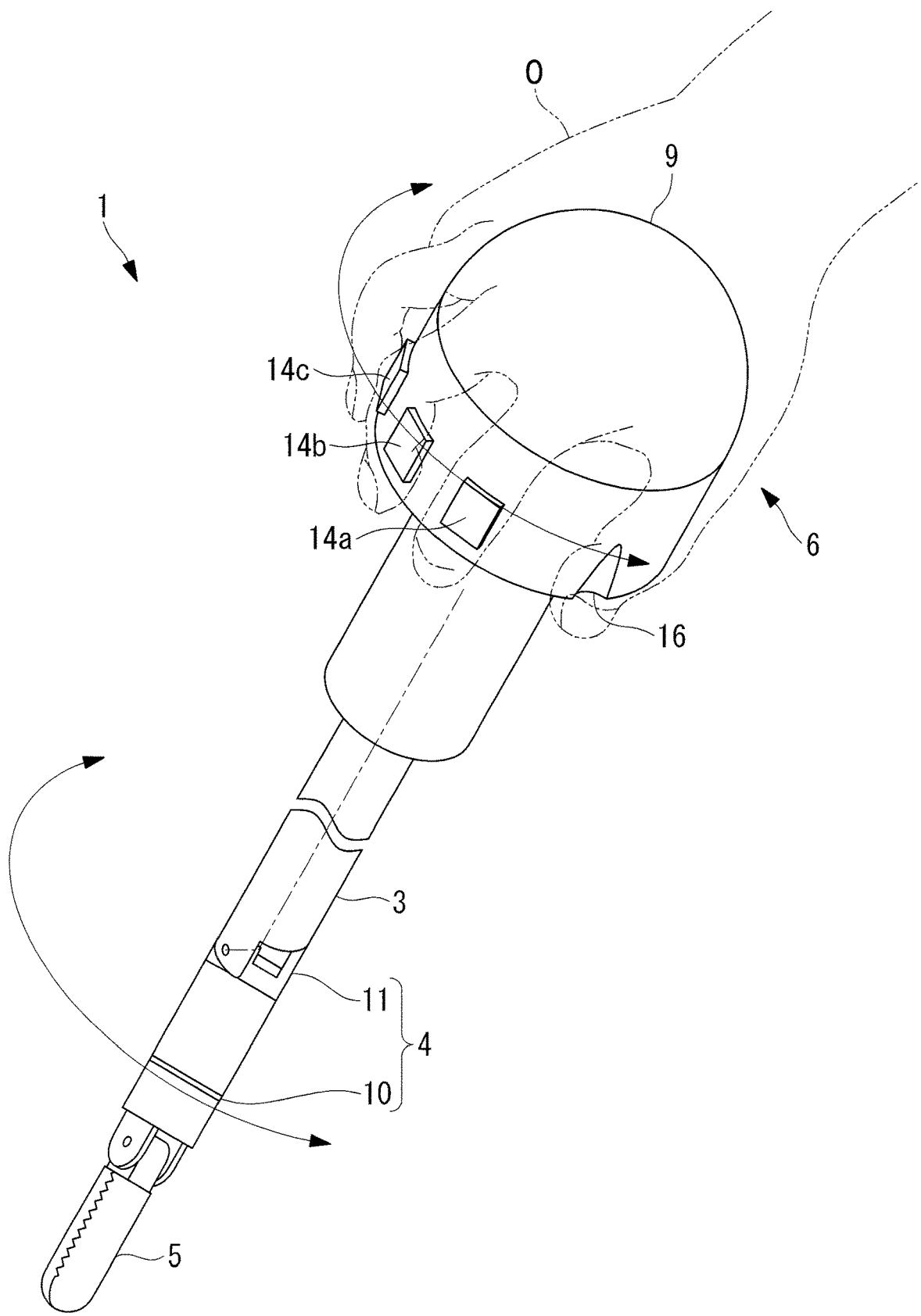
FIG. 5 is a perspective view for explaining a relationship between a twisting operation of a handle of the manipulator in FIG. 1 and the movement of the distal-end treatment section.

The bracket 3*a* and the handle 9 provided on the shaft 3 are engaged with each other such that they do not relatively rotate about the longitudinal axis of the shaft 3. As shown in FIG. 5, when the handle 9 is rotated by twisting the one hand gripping the handle 9, the rotational force is transmitted to the shaft 3 via the bracket 3*a*, causing the shaft 3 to rotate about its longitudinal axis.

Furthermore, the handle 9 is provided with three push buttons (second operating sections) 14*a*, 14*b*, and 14*c* separated from one another in the circumferential direction and disposed at positions where the index finger, the middle finger, and the ring finger of the one gripping hand are set when the operator O grips the handle 9 with one hand. As shown in FIG. 4, switches (sometimes referred to as second operation sections) 15*a*, 15*b*, and 15*c* that are disposed at positions corresponding to the push buttons 14*a*, 14*b*, and 14*c* and that are turned on and off by the respective push buttons 14*a*, 14*b*, and 14*c* are provided inside the handle 9.

An output from the encoder 13 and outputs from the switches 15*a*, 15*b*, and 15*c* are sent to the controller 8.

Furthermore, as shown in FIG. 3, the handle 9 is provided with grooves (recesses or protrusions) 16, which engage with the thumb and the little finger of the one gripping hand, at positions where the thumb and the little finger are set when the operator O grips the handle 9 with one hand.

The driving unit 7 includes two built-in motors at the proximal end of the shaft 3. One of the motors drives the bendable joint 11, whereas the other motor drives the rotatable joint 10. The driving forces from the respective motors are transmitted to the bendable joint 11 and the rotatable joint 10 via pulleys and wires (not shown).

The controller 8 receives the outputs from the encoder 13 and the three switches 15*a*, 15*b*, and 15*c* so as to control the motors of the driving unit 7 and the distal-end treatment section 5. In detail, when the handle 9 is tilted about the tilt shaft 12 relative to the shaft 3, the controller 8 drives one of the motors in accordance with the tilt angle and the tilting direction detected by the encoder 13 and sends, to one of the motors, a command signal for moving the bendable joint 11 in a tilting direction corresponding to the tilting direction of the handle 9 and by a tilt angle corresponding to the tilt angle of the handle 9.

Furthermore, the controller 8 sends, to the other motor, a command signal for moving the rotatable joint 10 in a rotational direction and by a rotational angle in accordance with outputs from the switches 15*a* and 15*c* corresponding to the push buttons 14*a* and 14*c* at the opposite ends of the three arranged push buttons 14*a*, 14*b*, and 14*c*. For example, in a case where the handle 9 is gripped with the right hand, the rotatable joint 10 is rotated counterclockwise when looking toward the distal end by pushing the push button 14*a* with the index finger, or the rotatable joint 10 is rotated clockwise by pushing the push button 14*c* with the ring finger. The motors are rotated only during the time during which the push buttons 14*a* and 14*c* are pushed.

Furthermore, the controller 8 sends, to the distal-end treatment section 5, a command signal for actuating the distal-end treatment section 5 in accordance with an output from the switch 15*b* corresponding to the middle push button 14*b* among the three arranged push buttons 14*a*, 14*b*, and 14*c*. In a case where the distal-end treatment section 5 is gripping forceps, the gripping forceps are closed when the push button 14*b* is pushed. In a case where the distal-end treatment section 5 is energy forceps, electricity is applied to the energy forceps when the push button 14*b* is pushed.

The operation of the manipulator 1 according to this embodiment having the above-described configuration will be described below.

As shown in FIG. 1, in order to medically treat the affected area B inside the body by using the manipulator 1 according to this embodiment, the shaft 3 is inserted from the distal end of the manipulator 1 into a through-hole of the trocar 2 pierced through the skin A, so that the distal-end treatment section 5 and the distal-end articulated section 4 are disposed inside the body.

In this state, the operator O grips the handle 9 with the right hand, as shown in FIG. 3, while viewing a monitor to check an image acquired by an endoscope (not shown) additionally inserted in the body, and sets the index finger, the middle finger, and the ring finger of the right hand respectively along the push buttons 14*a*, 14*b*, and 14*c* disposed on the outer periphery of the handle 9.

Because the handle 9 is attached to the shaft 3, moving the handle 9 can cause the shaft 3 to move along its longitudinal axis or the shaft 3 to move so as to change the tilt angle with respect to the trocar 2 serving as a fulcrum, as indicated by arrows in FIG. 1.

In other words, by moving the shaft 3, the position of the distal-end articulated section 4 disposed at the distal end of the shaft 3 and the position of the distal-end treatment section 5 fixed to the distal end of the distal-end articulated section 4 can be adjusted.

Furthermore, because the handle 9 and the shaft 3 are engaged with each other around the longitudinal axis of the shaft 3, the operator O may rotate the handle 9, like rotating a dial, with the right hand so as to rotate the shaft 3 about its longitudinal axis, as shown in FIG. 5. Accordingly, the distal-end articulated section 4 provided at the distal end of the shaft 3 and the distal-end treatment section 5 fixed to the distal end of the distal-end articulated section 4 can be rotated about the longitudinal axis of the shaft 3.

Figure 6:
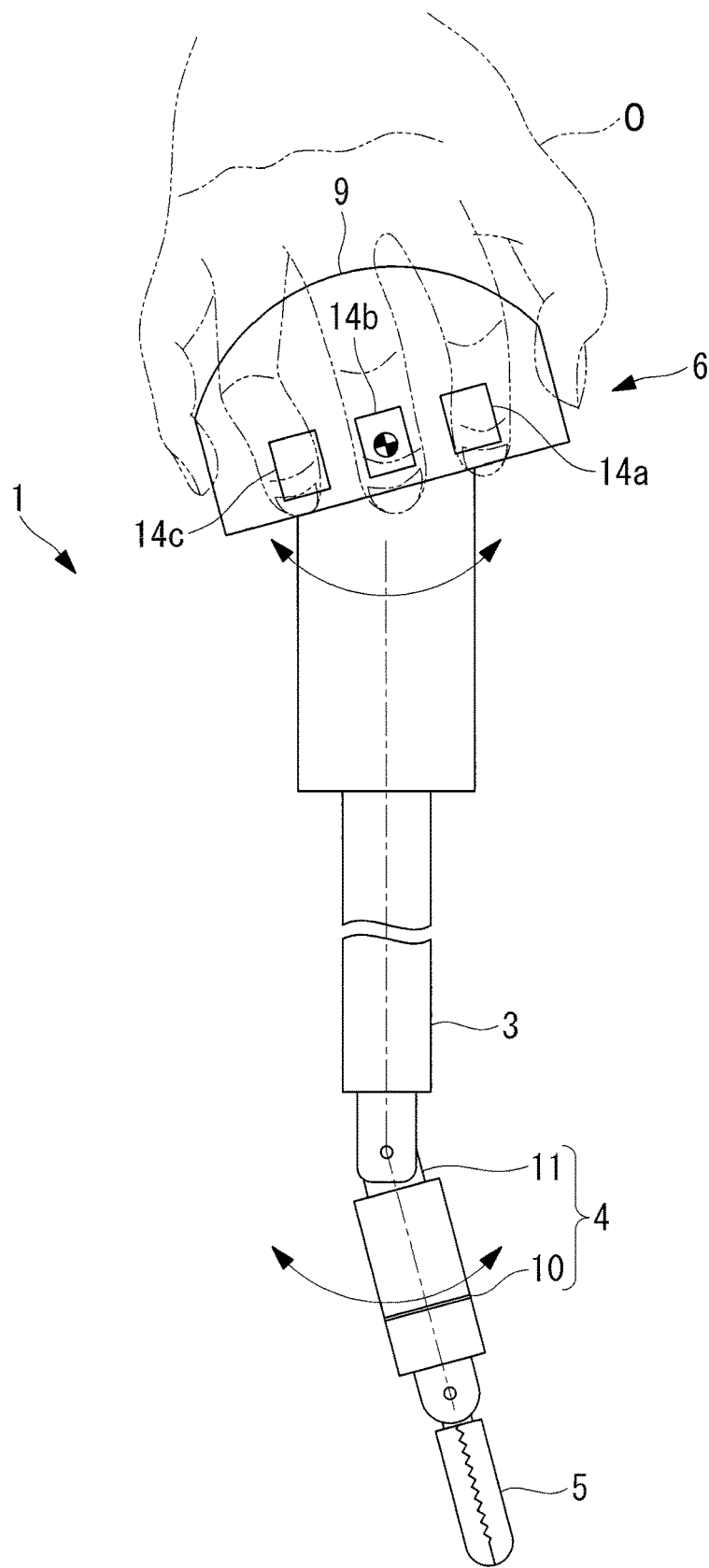
FIG. 6 is a plan view illustrating a relationship between a tilting operation of the handle of the manipulator in FIG. 1 and the movement of the distal-end articulated section.

Furthermore, as shown in FIG. 6, the operator O may rotate the wrist of the right hand gripping the handle 9, like twisting the forearm about its axis, so as to tilt the handle 9 about the tilt shaft 12 relative to the shaft 3. Thus, the tilt angle of the handle 9 relative to the shaft 3 is detected by the encoder 13, and the controller 8 controls one of the motors so as to tilt the bendable joint 11 of the distal-end articulated section 4 based on the detected tilt angle. Accordingly, the orientation of the distal-end treatment section 5 can be changed in the tilting direction of the bendable joint 11.

Moreover, the operator O can push the push button 14*a* with the index finger of the right hand gripping the handle 9 so as to rotate the rotatable joint 10 counterclockwise when looking toward the distal end, or can push the push button 14*c* with the ring finger of the right hand so as to rotate the rotatable joint 10 clockwise when looking toward the distal end. Accordingly, the distal-end treatment section 5 can be rotated counterclockwise or clockwise about the central axis thereof.

Then, in the state where the position and orientation of the distal-end treatment section 5 relative to the affected area B are adjusted, the operator O pushes the push button 14b with the middle finger of the right hand gripping the handle 9 so as to actuate the distal-end treatment section 5, whereby the affected area B is medically treated.

In this case, in the manipulator 1 according to this embodiment, the axis about which the handle 9 is tilted relative to the shaft 3 and the axis of the bendable joint 11 about which the distal-end treatment section 5 is tilted relative to the shaft 3 are substantially parallel to each other, so that the tilting of the handle 9 and the tilting of the distal-end treatment section 5 are able to completely correspond with each other. As a result, the operation for changing the orientation of the distal-end treatment section 5 can be performed intuitively, thereby allowing for improved ease of operation.

In particular, the orientation of the palm of the right hand gripping the handle 9 can be substantially aligned with the direction of the central axis of the distal-end treatment section 5, thereby realizing high intuitiveness.

Furthermore, because the axis of the tilt shaft 12 for tilting the handle 9 is disposed in the right hand gripping the handle 9, the handle 9 can be operated simply by rotating the wrist of the right hand about the longitudinal axis of the forearm while keeping the orientation of the forearm substantially fixed. Therefore, tilting the handle 9 only causes a couple to be generated with respect the axis of the tilt shaft 12 serving as the center, so that a force for tilting the shaft 3 with respect to the trocar 2 serving as a fulcrum does not have to be generated. On the other hand, when tilting the shaft 3 with respect to the trocar 2 serving as a fulcrum, a moment is applied to the shaft 3 by moving the entire forearm while keeping the wrist of the right hand gripping the handle 9 fixed relative to the forearm, so that the shaft 3 can be tilted.

Specifically, the manipulator 1 according to this embodiment is advantageous in that the operation for tilting the distal-end treatment section 5 relative to the distal end of the shaft 3 and the operation for tilting the shaft 3 itself can be performed independently without interference therebetween, thereby preventing the distal-end treatment section 5 from moving in an unintended direction and enabling improved ease of operation.

Figure 7:
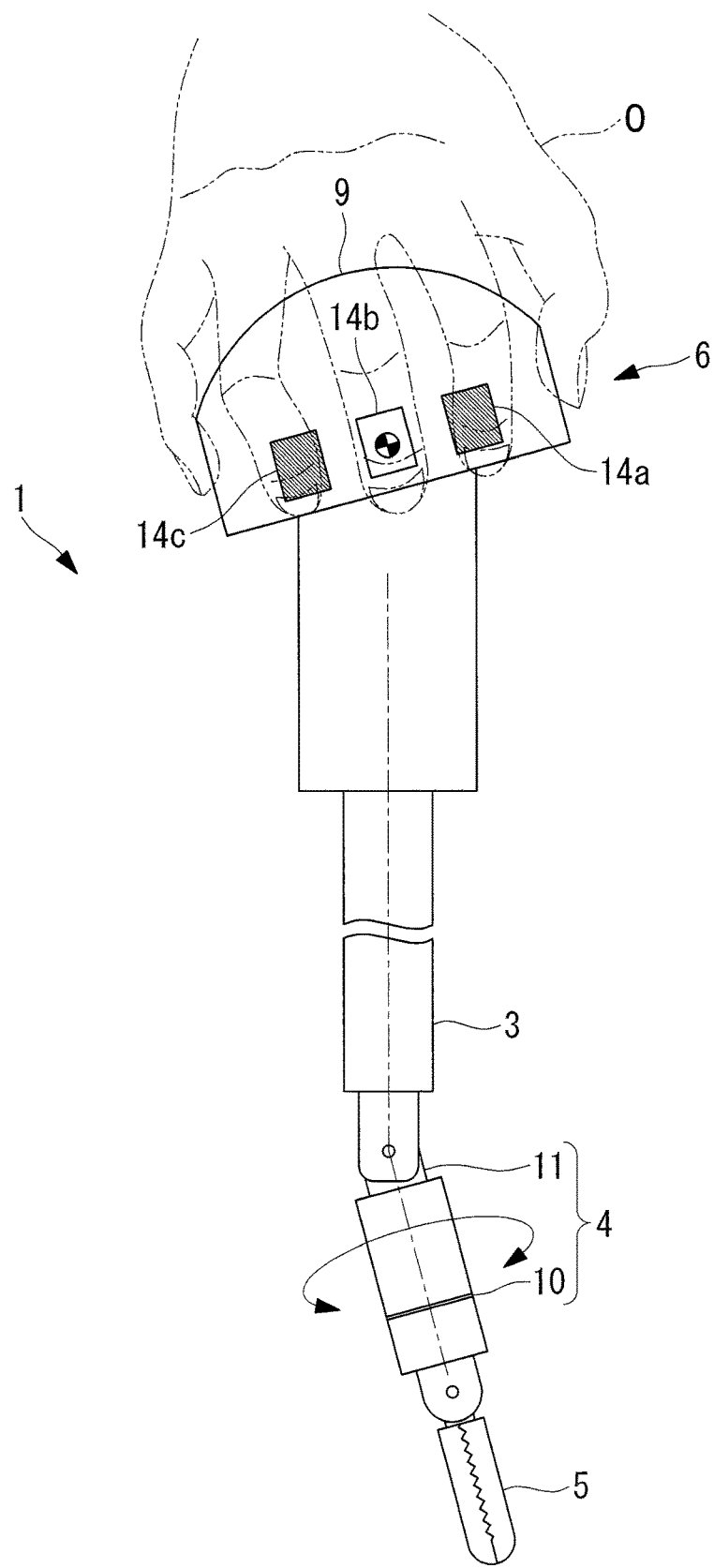
FIG. 7 is a plan view illustrating a relationship between an operation performed on switches provided on the handle of the manipulator in FIG. 1 and the movement of the distal-end articulated section.

Furthermore, in the manipulator 1 according to this embodiment, the shaft 3 itself can be rotated about its longitudinal axis by rotating the handle 9 like a dial with the right hand gripping the handle 9, and the rotatable joint 10 of the distal-end articulated section 4 can be rotated by operating the push buttons 14a, 14b, and 14c, as shown in FIG. 7. Specifically, the two operations are completely different from each other and therefore do not interfere with each other, thus eliminating the need to switch fingers or re-grip the handle. This also is advantageous in terms of preventing the distal-end treatment section 5 from moving in an unintended direction and enabling improved ease of operation.

Because the movement of the rotatable joint 10 for simply rotating the distal-end treatment section 5 about its central axis has a low degree of contribution to the change in orientation of the distal-end treatment section 5, intuitiveness is not impaired by the operation of the push buttons 14a, 14b, and 14c. In addition, because the positions of the push buttons 14a, 14b, and 14c are set in correspondence with the rotational directions of the rotatable joint 10, the manipulator 1 according to this embodiment is advantageous in that high intuitiveness can be obtained even with a similar structure.

Furthermore, because the thumb and the little finger of the right hand are hooked onto the grooves 16 provided in the handle 9, slipping is prevented when rotating the handle 9 like a dial, thereby enabling improved ease of operation.

Although the handle 9 has a substantially semispherical shape in this embodiment, the shape is not limited to this, and another freely-chosen shape may be employed.

Figure 8:
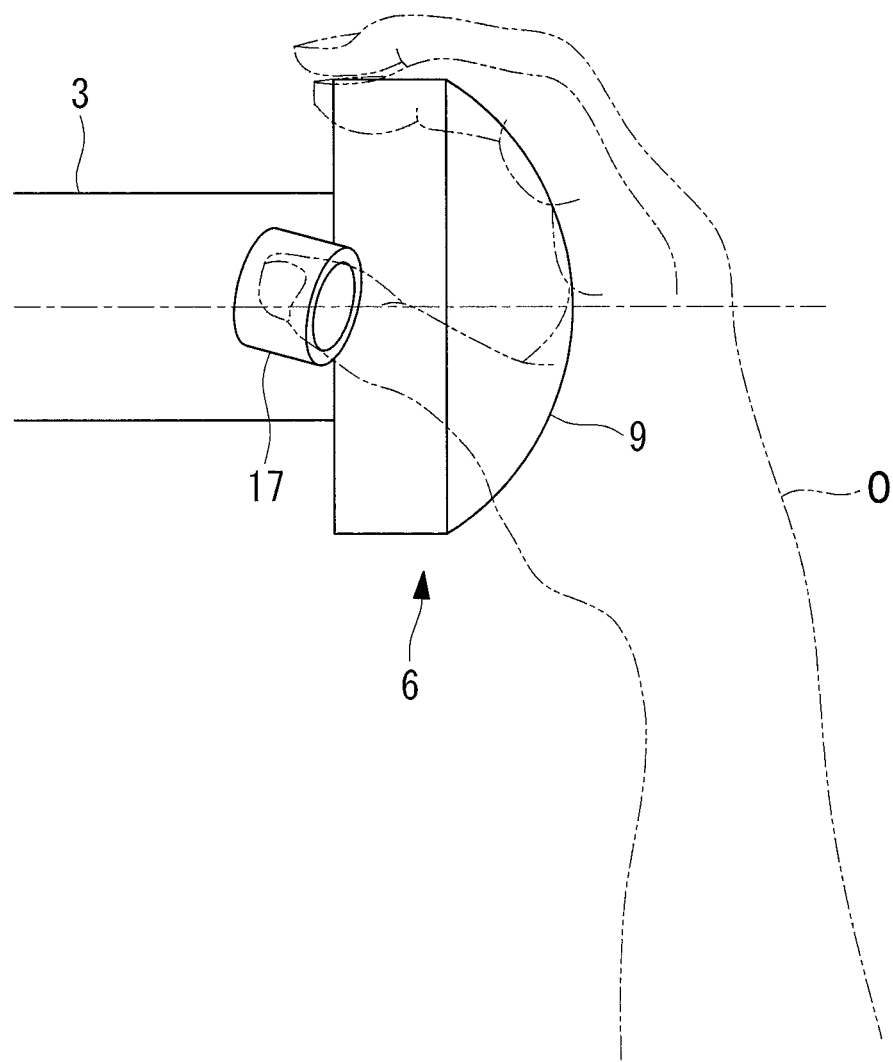
FIG. 8 illustrates a modification of the manipulator in FIG. 1 and is a front view of the proximal-end operating section.

Moreover, although the grooves 16 that engage with the thumb and the little finger are provided in the handle 9, the grooves 16 may be replaced with protrusions. Additionally, ring members 17 in which the thumb and the little finger are fitted when the handle 9 is gripped may be provided, as shown in FIG. 8. This can further eliminate slippage between the hand and the handle 9.

Furthermore, although the tilt shaft 12 of the handle 9 is disposed in a direction orthogonal to the longitudinal axis of the shaft 3, the tilt shaft 12 may alternatively be disposed in a direction intersecting the longitudinal axis of the shaft 3 at a freely-chosen angle.

Moreover, although the handle is gripped with the right hand in this embodiment, the embodiment may be applied to a case where the left hand is used for the operation. In that case, the push button 14a for rotating the rotatable joint 10 counterclockwise may be disposed at the position where the ring finger of the left hand is to be set, and the push button 14c for rotating the rotatable joint 10 clockwise may be disposed at the position where the index finger of the left hand is to be set.

The inventor has arrived at the following aspects of the present invention.

An aspect of the present invention provides a manipulator including: an elongated shaft; a distal-end treatment section disposed at a distal end side of the shaft; a distal-end articulated section having a rotatable joint and a bendable joint for moving the distal-end treatment section relative to the shaft, the bendable joint being disposed at a shaft side relative to the rotatable joint; and a proximal-end operating section that is disposed at a proximal end side of the shaft and that is to be operated by an operator, wherein the bendable joint has an axis intersecting a longitudinal axis of the shaft, wherein the rotatable joint has an axis that intersects the axis of the bendable joint and that is substantially aligned with a central axis of the distal-end treatment section, and wherein the proximal-end operating section includes a first operating section to be gripped by one hand of the operator and a second operating section provided in the first operating section, wherein the first operating section causes the bendable joint to move in accordance with a rotational angle of a wrist of the one hand about an axis intersecting the longitudinal axis of the shaft, and the second operating section is operated by a finger of the one hand so as to cause the rotatable joint to move.

According to this aspect, when the operator operates the first operating section of the proximal-end operating section and rotates the wrist about the axis intersecting the longitudinal axis of the shaft, the bendable joint of the distal-end articulated section disposed at the distal end of the shaft causes the distal-end treatment section to tilt about the axis intersecting the longitudinal axis of the shaft in accordance with the rotational angle. Moreover, the operator operates the second operating section of the proximal-end operating section and moves the finger of the hand operating the first operating section, thereby rotating the rotatable joint of the distal-end articulated section disposed at the distal end of the shaft.

In this case, since the rotational angle of the wrist of the one hand operating the first operating section corresponds to the amount of change in the orientation of the distal-end treatment section caused by moving the bendable joint, the distal-end treatment section can be operated intuitively. On the other hand, because the rotatable joint causes the distal-end treatment section to rotate about the axis substantially aligned with the central axis of the distal-end treatment section, the orientation of the distal-end treatment section is not changed by the rotation of the rotatable joint. Therefore, the distal-end treatment section can be rotated by operating the second operating section with a finger without changing the position of the one hand operating the first operating section or without impairing the intuitiveness. Moreover, because the rotating motion of the distal-end treatment section is not related to the rotating motion of the wrist, the distal-end treatment section can be moved as intended by the operator without interference with the rotating motion about the longitudinal axis of the shaft.

In the above aspect, the first operating section may include a handle that is gripped by the operator so that the longitudinal axis of the shaft extends through a palm of the one hand.

With this configuration, when the operator grips the handle, the palm of the one hand gripping the handle is set at a position through which the longitudinal axis of the shaft extends. When the orientation of the palm is changed in this state by rotating the wrist of the one hand gripping the handle, the distal-end treatment section can be tilted in correspondence with the orientation of the palm. This enables an operation with higher intuitiveness.

Furthermore, in the above aspect, the axis about which the handle is tilted may be disposed in the one hand gripping the handle.

With this configuration, when changing the orientation of the palm of the one hand gripping the handle, the wrist can be swiveled while hardly changing the position of the forearm of that arm. Since operating the first operating section would only cause a couple to occur about the axis but would not cause a force that swivels the shaft to occur, the operation for tilting the distal-end treatment section and the operation for swiveling the shaft can be performed independently without interference therebetween.

Furthermore, in the above aspect, the handle may be connected to a proximal end of the shaft such that the handle can rotate the shaft about the longitudinal axis.

Accordingly, by using the one hand gripping the handle to rotate the handle about the longitudinal axis of the shaft, the shaft can be rotated about the longitudinal axis, so that the distal-end treatment section at the distal end of the shaft can be rotated about the longitudinal axis of the shaft.

Furthermore, in the above aspect, an outer peripheral surface of the handle may have a recess or protrusion onto which a finger of the one hand gripping the handle is hooked.

Accordingly, when the operator grips the handle, the finger of the one gripping hand becomes hooked onto the recess or protrusion. Thus, when the handle is rotated about the longitudinal axis, force can be applied more reliably.

Furthermore, in the above aspect, the second operating section may be a switch that is disposed at a position where the switch is operable by the finger of the one hand when the handle is gripped with the one hand.

Accordingly, when the operator grips the handle, the switch is disposed at the position corresponding to the finger of the one gripping hand. Thus, in the state where the handle is gripped, the distal-end treatment section can be rotated about its central axis by simply operating the switch.

The aforementioned aspects are advantageous in that it can prevent an operation for rotating a treatment section at the distal end of a shaft from interfering with other operations and enables intuitive control of the position and orientation of the treatment section.

REFERENCE SIGNS LIST 1 manipulator
3 shaft
4 distal-end articulated section
5 distal-end treatment section
6 proximal-end operating section
9 handle (first operating section)
10 rotatable joint
11 bendable joint
14a, 14b, 14c push buttons (second operating sections)
15a, 15b, 15c switches (sometimes referred to as second operating sections)
16 grooves (recesses or protrusions)
O operator

The invention claimed is:
1. A manipulator comprising:
a shaft;
a distal-end treatment section disposed at a distal end side of the shaft and configured to medically treat an object;
a bendable joint provided in the shaft and has a first axis which is substantially orthogonal to a longitudinal axis of the shaft, the bendable joint being configured to tilt the distal-end treatment section around the first axis;
a rotatable joint provided in the shaft at a distal-end treatment section side relative to the bendable joint, the rotatable joint having a second axis which is substantially aligned with a central axis of the distal-end treatment section, the rotatable joint being capable of rotating the distal-end treatment section around the second axis; and
a handle disposed at a proximal end side of the shaft, the handle being connected to the shaft so that the handle can be tilted about a tilting axis, the handle comprising a switch;
wherein the tilting axis is positioned in the handle and substantially parallel to the first axis,
wherein the manipulator further comprises:
a first motor which moves the bendable joint around the first axis in accordance with tilting of the handle around the tilting axis; and
a second motor which moves the rotatable joint about the second axis in accordance with input to the switch;
wherein the switch is disposed at a position where the switch is operable by a finger of one hand when the handle is gripped with the one hand.
2. The manipulator according to claim 1, wherein the handle comprises a first finger-hooking portion and a second finger-hooking portion disposed at substantially opposite positions in a circumference direction of the handle, for enabling the handle to be rotated about the longitudinal axis of the shaft.

* * * * *